United States Patent [19]

Ogawa et al.

[11] Patent Number: 5,072,736
[45] Date of Patent: Dec. 17, 1991

[54] NON-INVASIVE AUTOMATIC BLOOD PRESSURE MEASURING APPARATUS

[75] Inventors: Keikitsu Ogawa, Tokorozawa; Takeda Sunoa, both of Ichikawa; Mitsushi Hyogo, Niiza; yoshiaki Shindo, Higashikurume, all of Japan

[73] Assignee: Nihon Kohden Corporation, Tokyo, Japan

[21] Appl. No.: 467,780

[22] Filed: Jan. 19, 1990

[51] Int. Cl.$^5$ .............................................. A61B 5/02
[52] U.S. Cl. .................................. 128/680; 128/691; 128/661.08
[58] Field of Search ........... 128/672, 677, 680, 661.01, 128/661.08, 661.09, 661.1, 691, 681–689

[56] References Cited

U.S. PATENT DOCUMENTS

| | | | |
|---|---|---|---|
| 4,205,688 | 6/1980 | Hauser et al. | 128/694 |
| 4,412,545 | 11/1983 | Okino et al. | 128/691 |
| 4,592,366 | 6/1986 | Sainomoto et al. | 128/680 |
| 4,730,621 | 3/1988 | Stott | 128/680 |
| 4,867,171 | 9/1989 | Yamaguchi | 128/680 |
| 4,880,013 | 11/1989 | Chio | 128/681 |
| 4,961,429 | 10/1990 | Chang et al. | 128/680 |

FOREIGN PATENT DOCUMENTS 3605194 8/1987 Fed. Rep. of Germany ...... 128/672

Primary Examiner—Stephen C. Pellegrino
Assistant Examiner—Robin R. Longo
Attorney, Agent, or Firm—Hoffmann & Baron

[57] ABSTRACT

A non-invasive automatic blood pressure measuring apparatus consisting of a blood flow meter non-invasively detecting the blood flow of the arteries on the proximal or distal side of the cuff, a blood flow standing up point detecting means detecting the standing up point of the blood flow signal output from the blood flow meter in the decompression process of the internal pressure in the cuff and a blood flow returning point detecting means detecting the returning point of the blood flow signal to the steady state in the further successive decompression process, and detecting the internal pressure in the cuff of the standing up point as the maximal value of the blood pressure and the internal pressure in the cuff of the returning point as the minimal value of the blood pressure.

2 Claims, 3 Drawing Sheets

NON-INVASIVE AUTOMATIC BLOOD PRESSURE MEASURING APPARATUS

BACKGROUND OF THE INVENTION

1. Field of the Invention

The present invention relates to a non-invasive automatic blood pressure measuring apparatus for non-invasively detecting the maximal blood pressure and the minimal blood pressure in the depressing process after attaching a cuff at a part of the body and compressing.

2. Description of the Prior Art

In this kind of automatic blood pressure measuring apparatus, there are two kinds of apparatuses; a first type which detects Korotkov sounds by a microphone in the depressing process and measures the internal pressure of the cuff at the start and the termination of this sound according to the Korotkov sound recognizing method, and a second type which detects a pulse wave caused by the pulsation of the artery as a vibration upon the internal pressure of the cuff and measures the blood pressure based on the change of this vibration according to an oscillometric method.

However, the apparatus of the former method is easily affected by noises. In addition, there is a problem in its measuring precision because there are cases that Korotkov sounds sometimes fade away or do not fade out even if blood pressure is minimal. In the latter method, although the problems caused by the lack of stability of the generation of Korotkov sounds have been solved, there still remains a problem with its measuring precision: since the pulse wave is detected as an internal pressure change in the cuff, the pulse waves contacting the cuff at different points varied in the direction of the width of the cuff are detected with add operation. In addition, since the detection of minimal blood pressure from the vibration itself is difficult, and it is supposed from the operation using the mean value of the blood pressure, a problem also remains in its measuring precision.

SUMMARY OF THE INVENTION

The purpose of the present invention is to provide a non-invasive automatic blood pressure measuring apparatus based on a new system which is capable of measuring blood pressure with greater accuracy.

To accomplish this purpose, the non-invasive automatic blood pressure measuring apparatus of the present invention detects a standing up point of a blood flow signal output from a blood flow meter in the depressing process of the internal pressure of the cuff, holds the internal pressure of the cuff at this standing up point at the time blood flow is at the maximal value of blood pressure, detects a returning point at the time blood flow signal reaches the steady state in the depressing process, and holds the internal pressure of the cuff of this returning point at the time blood flow is at the minimal value of blood pressure.

According to the present invention, both maximal and minimal blood pressures can be measured with high accuracy since the values of both blood pressures can be directly determined from the pulse signals whose vibrating amplitude is more correctly correlated with the depression of the internal pressure of the cuff and which has a high S/N ratio and stability, by non-invasively detection and signal processing of the blood flow.

DESCRIPTION OF THE PREFERRED EMBODIMENTS

Figure 1:
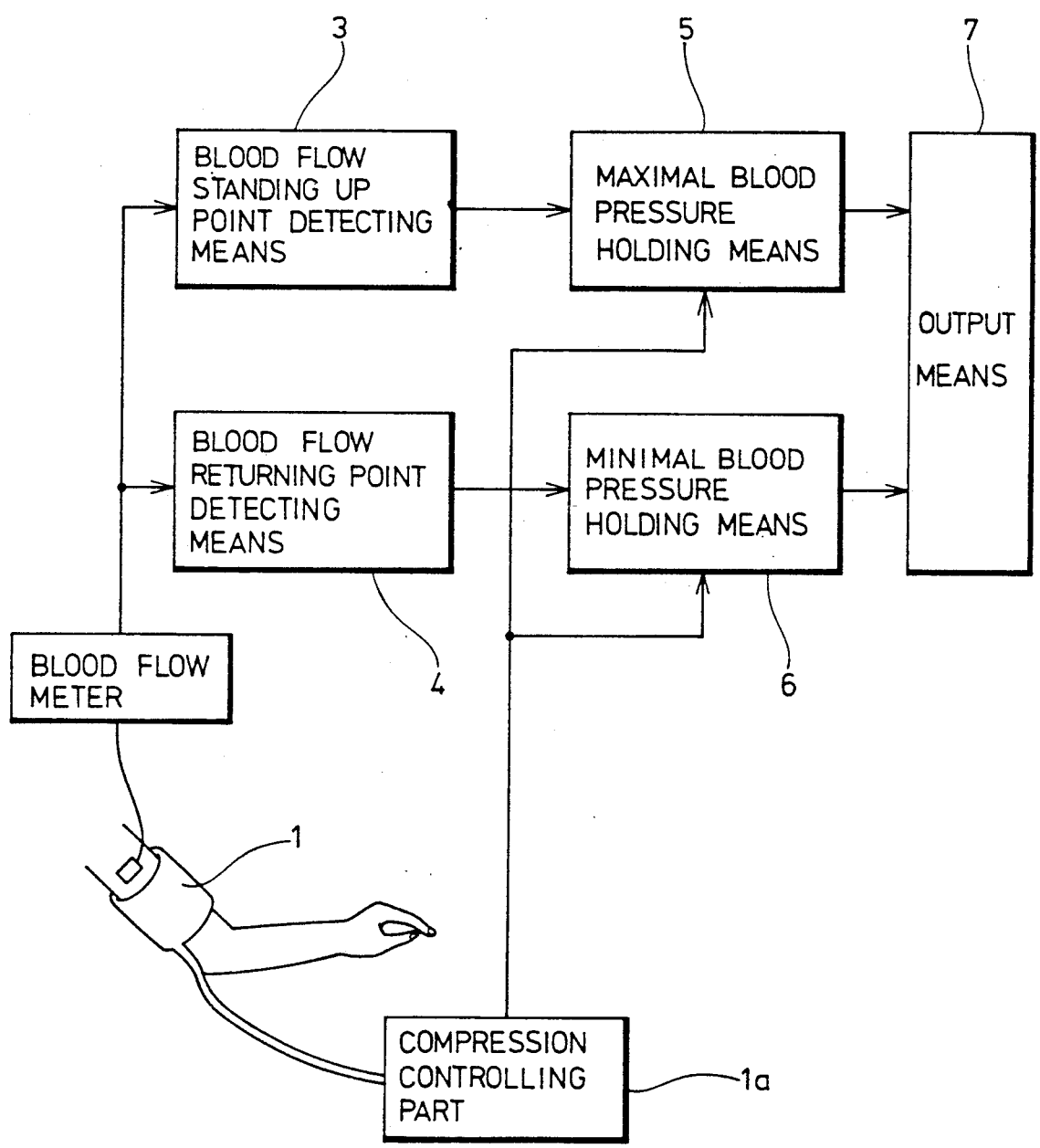
FIG. 1 shows a composition of the non-invasive automatic blood pressure measuring apparatus of a theoretical embodiment of the present invention.

FIG. 1 shows a theoretical embodiment of the present invention.

As shown in this figure, the non-invasive automatic blood pressure measuring apparatus of this embodiment consists of a cuff 1 being depressed for measuring after being attached to a part of the body and compressed by a compression controlling part 1a, a blood flow meter 2 non-invasively detecting the blood flow of the arteries on the proximal or distal side of this cuff 1, a blood flow standing up point detecting means 3 detecting the standing up point of the blood flow signal output from the blood flow meter 2 in the depressing process of the internal pressure in the cuff 1, a blood flow returning point detecting means 4 detecting the returning point of the blood flow signal to the steady state in the further successive depressing process, a maximal blood pressure holding means 5 holding the internal pressure in the cuff of the standing up point as the maximal value of the blood pressure, a minimal blood pressure holding means 6 holding the internal pressure in the cuff of the returning point as the minimal value of the blood pressure and an output means 7 displaying or printing out these holding maximal and minimal values of the blood pressures.

A blood flow standing up point detecting means and a blood flow returning point detecting means can be adapted to smooth the pulse component of the detected blood flow signal so as to derive an average amplitude blood flow signal. Based on this computed average amplitude blood flow signal, a standing up point and returning point of the blood flow signal can be detected.

At the time of measuring the blood pressure, the cuff 1 is decompressed for measuring the blood pressure after being compressed by the compression controlling part 1a. In this decompression process (shown in FIG. 2 (a)), the blood flow signal (shown in FIG. 2 (b)) detected by the blood flow meter gradually increases in its vibration amplitude from the hemostasis and its vibration amplitude reaches its maximum in the average blood pressure region. And it gradually reaches the steady state which the pulsations of constant vibration amplitude repeat in a normal flow direction when the depression is further continued. The blood flow standing up point detecting means 3 detects the standing up point of the blood flow signal indicating the initiation of the blood flow from the hemostasis and causes the maximal blood pressure holding means 5 to hold the pressure of the internal pressure in the cuff 1 as the maximal value of the blood pressure.

On the other hand, the blood flow returning point detecting means 4 detects the point where the vibrating amplitude returns to the steady state as the blood flow returning point, causes the minimal blood pressure holding means 6 to hold the minimal value of the blood pressure and causes the output means 7 display them.

Figure 2:
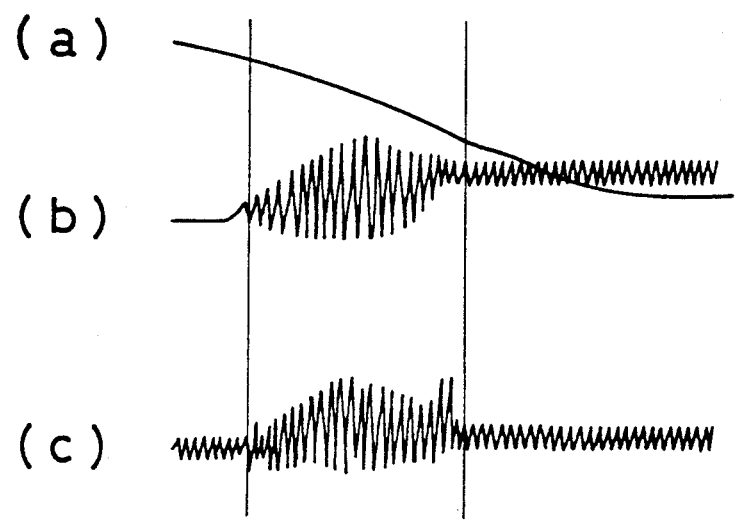
FIG. 2 explains the action of the embodiment shown in FIG. 1.

Incidentally, the pulsation caused by the vibration of the internal pressure in the cuff according to the oscillometric method is inferior in S/N ratio and in the correlativity between the change in the internal pressure in the cuff when compared with the blood flow signal, as shown in FIG. 2 (c).

Figure 3:
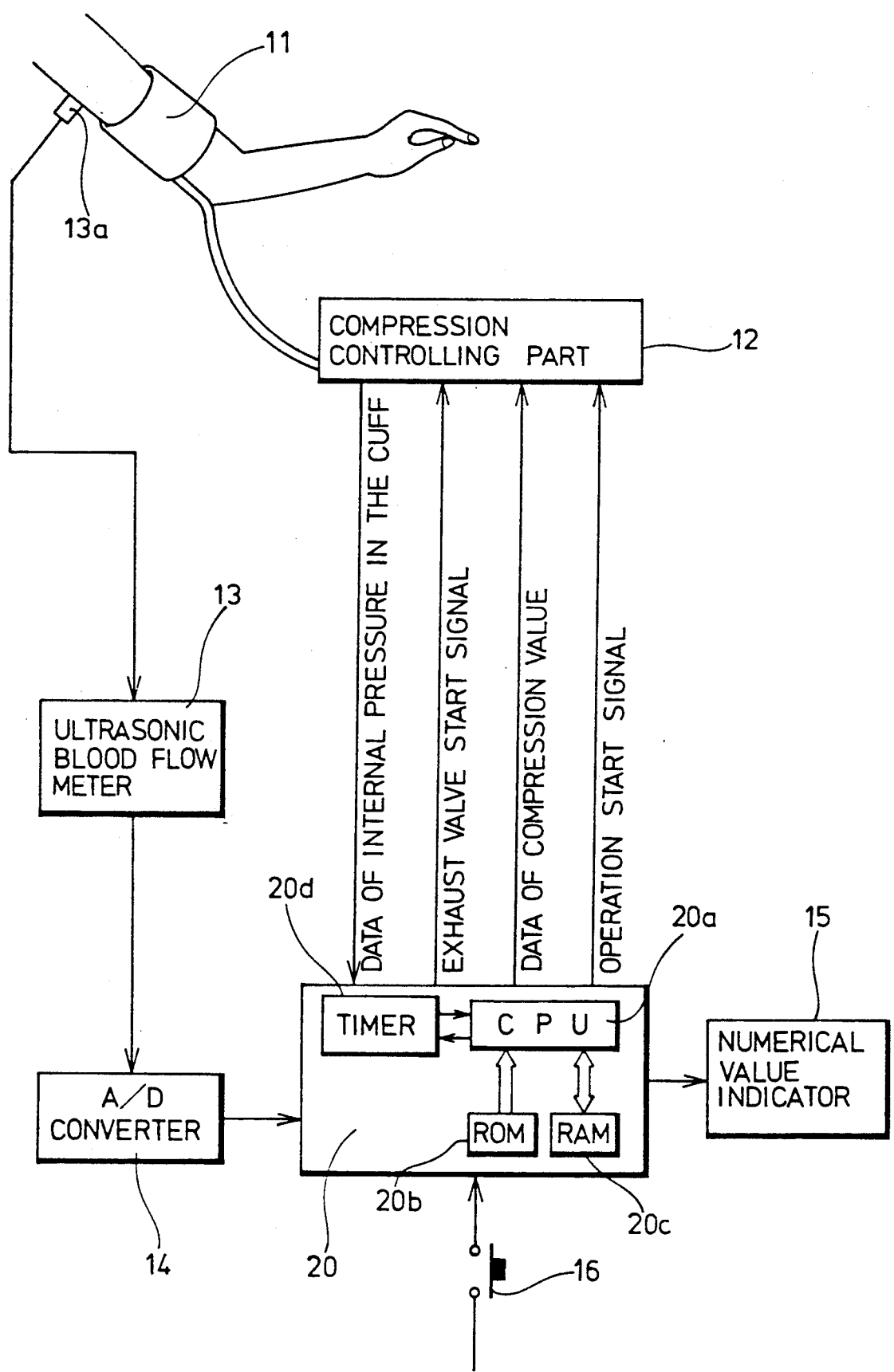
FIG. 3 shows a composition of the non-invasive automatic blood pressure measuring apparatus of a detailed embodiment of the present invention.

FIG. 3 shows a circuit composition of the non-invasive automatic blood pressure measuring apparatus of the embodiment of the present invention using a microcomputer 20. In this figure, a cuff 11 attached to the upper arm of the subject is compressed or decompressed by the compression controlling part 12 as is generally known. Reference numeral 13 denotes an ultrasonic blood flow meter having a probe 13a set at the upper arm to which the proximal side of the cuff 11 is adjacent. Reference numeral 14 and 15 denote an A/D converter digitizing the blood flow signal and a numerical value indicator for the maximal and minimal blood pressures, respectively. A recorder can be used instead of this output means. Reference numeral 16 denotes a starting switch.

A compression controlling part 12 gradually exhausting decompresses the compressed air by controlling an exhaust valve after compressing the air to the specified pressure with a pressure pump according to the instruction of the microcomputer 20, and opens to full width of the exhaust valve similarly according to the instruction which is sent from the microcomputer 20 when the minimal blood pressure is detected. During this time, the data of the internal pressure in the cuff detected by the built-in pressure sensor is sent to the microcomputer 20.

The microcomputer 20 is operated by CPU20a according to the program stored in ROM20b, gives and receives control signals or data to or from the aforementioned parts 12, 14 to 16 through the built-in I/O port and works as the blood flow standing up point and the returning point detecting means and the maximal and the minimal blood pressure holding means according to the present invention. Eventually, RAM20c time-serially memorizes the amplitude data (FIG. 4 (a)) and the data regarding the internal pressure in the cuff (FIG. 4 (b)), and CPU20a performs the following operating processing in accordance with the program stored in the ROM20b taking in the timer signal of a timer 20d based on these memorized data.

Figure 4:
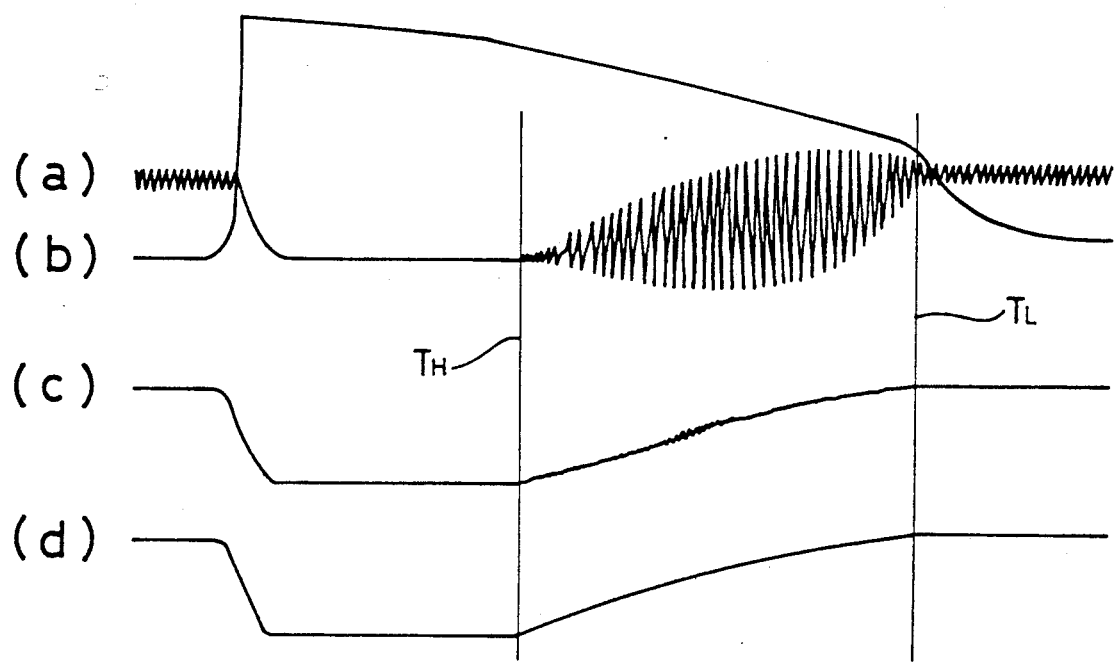
FIG. 4 explains the action of the embodiment shown in FIG. 3.

That is, CPU20a first prepares the averaged amplitude data (FIG. 4 (c)) by detecting the maximum and the minimum values of the taken amplitude data one after another, and causes RAM20c to memorize this averaged amplitude data by making it similarly correspond to the internal pressure in the cuff in point of time. Next, CPU20a prepares the moving averaged amplitude data (FIG. 4 (d)) for, for example, 4 seconds at 0.1 second intervals and again causes RAM20c to memorize it by making it correspond to the internal pressure in the cuff in point of time. Furthermore, it also prepares the moving averaged amplitude data before the initiation of compression, calculates its 1% value and sends the operation start signal to the compression controlling part 12. And CPU20a detects the time that the moving averaged data in the decompression process rises from the hemostasis to the aforementioned 1% value as the blood flow standing up point $T_H$, holds the internal pressure in the cuff during this time and causes the indicator 15 to indicate this pressure as the maximal blood pressure. Next, it prepares the increase rate of the moving averaged data of the blood flow signal in the successive decompression process, i.e., the differential data, measures the time that it takes for this increase rate to decrease to 1% of its maximal value after increasing once as the blood flow returning time $T_L$, holds the internal pressure in the cuff during this time and causes the indicator 15 to indicate this pressure as the minimal blood pressure.

Next, the action of the thus constructed non-invasive automatic blood pressure measuring apparatus will be explained.

An ultrasonic blood flow meter 13 non-invasively detects the blood flow when its probe 13a is applied to the artery part on the distal side of the cuff 11. When the start switch 16 is turned on, the microcomputer 20 is initialized, takes in the digitized blood flow signal before the initiation of compression and prepares the moving averaged amplitude data. And it initiates the decompression after compressing the cuff 1 to the specified compression value taking the specified time. The microcomputer 20 performs averaging the maximum and the minimum values of the vibrating blood flow signal and moving averaging this averaged data in this depressing process as described above (FIG. 4 (a) to (d)). In parallel with this operational process, the microcomputer 20 further detects the blood flow standing up point $T_H$ and the blood flow returning point $T_L$ with the aforementioned processing method, detects and holds their corresponding internal pressure in the cuff as the maximal and the minimal blood pressures and causes the indicator 15 to indicate them. After detection of the minimal blood pressure, it rapidly decreases the internal pressure in the cuff by opening the exhaust valve to its full width and terminates the measuring.

According to the blood pressure measurement of this blood flow detecting system, the maximal and the minimal blood pressures can be detected with high precision directly from the blood flow signal because the amplitude of the pulsation signal changes smoothly corresponding to the internal pressure in the cuff and it imitates the depression of the internal pressure in the cuff with high precision by the moving average.

As for the blood flow detecting system of the present invention, it is supposed that the system can also directly prepare the envelope curve with moving averaging the maximum and the minimum values of the vibrating waveform of the blood flow signal, for example by 5, without smoothing them once, detect the time that they exceed the slightly increasing envelope curve level determined in advance from the hemostasis as the standing up point of the blood flow and detect the time they return to the slightly increasing envelope curve level determined in advance from the envelope curve level from the large pulsation of the average blood pressure region to the steady state as the returning point of the blood flow.

What is claimed is:

1. A non-invasive automatic blood pressure measuring apparatus comprising:
    a measuring cuff adapted for decompression after compression and attachment to a part of a body, the measuring cuff having a proximal side and a distal side;
    a blood flow meter non-invasively detecting the blood flow of the arteries on the proximal or distal side of said cuff.

a moving average blood flow signal detecting means calculating a moving average blood flow signal from the blood flow of the arteries on the proximal or distal side of said cuff, the average blood flow signal detecting means calculating a 1% average blood flow signal value representative of a blood flow standing up point and a 99% average blood flow signal value representative of a blood flow returning point;

a blood flow standing up point detecting means monitoring blood flow to detect the 1% average blood flow signal value during a decompression process of internal pressure on said cuff;

a blood flow returning point detecting means monitoring the blood flow to detect the 99% average blood flow signal value during a further decompression process of internal pressure on said cuff;

a maximal blood pressure holding means storing a maximal blood pressure value corresponding to the internal pressure in said cuff when the 1% average blood flow signal value is detected by the blood flow standing up point detecting means;

a minimal blood pressure holding means storing a minimal blood pressure value corresponding to the internal pressure in said cuff when the 99% average blood flow signal value is detected by the blood flow standing up point detecting means; and an output means indicating or printing out the stored maximal and minimal blood pressure values.

2. A non-invasive automatic blood pressure measuring apparatus comprising:

a measuring cuff adapted for decompression and compression and for attachment to a part of a patient's body, the measuring cuff having a proximal side and a distal side;

a blood flow meter non-invasively detecting the blood flow of a patient's artery on one of the proximal and distal side of the cuff, the blood flow meter providing an output signal corresponding to the blood flow measured through the artery;

a moving average blood flow signal calculating means responsive to the output signal from the blood flow meter, the moving average blood flow signal calculating means calculating a moving average blood flow value from the blood flow measured by the blood flow meter, and further calculating a 1% value corresponding to about 1% of the moving average blood flow value and representative of a blood flow standing up point and a 99% value corresponding to about 99% of the moving average blood flow value and representative of a blood flow returning point;

a blood flow standing up point detecting means responsive to the output signal of the blood flow meter, the blood flow standing up point detecting means detecting when the 1% value of blood flow is reached during a decompression process of the internal pressure in the cuff;

a blood flow returning point detecting means responsive to the output signal from the blood flow meter, the blood flow returning point detecting means detecting when the 99% value of blood flow is reached during a further decompression process of the internal pressure in the cuff;

maximal blood pressure holding means coupled to the blood flow standing up point detecting means, the maximal blood pressure holding means storing a maximal blood pressure value corresponding to the internal pressure in the cuff when the 1% value of blood flow is detected by the blood flow standing up point detecting means;

minimal blood pressure holding means coupled to the blood flow returning point detecting means, the minimal blood pressure holding means storing a minimal blood pressure value corresponding to the internal pressure in the cuff when the 99% value of blood flow is detected by the blood flow returning point detecting means; and output means coupled to the maximal and minimal blood pressure holding means, the output means indicating the stored maximal and minimal blood pressure values.

* * * * *